US012766132B2

(12) United States Patent
Patel et al.

(10) Patent No.: US 12,766,132 B2
(45) Date of Patent: Oct. 20, 2026

(54) LYOPHILIZED BENDAMUSTINE-CYCLODEXTRIN COMPOSITION

(71) Applicant: SOFTKEMO PHARMA CORP., Montreal (CA)

(72) Inventors: Kishore Patel, Pierrefonds (CA); William Dickheiser, Glen Mills, PA (US)

(73) Assignee: SOFTKEMO PHARMA CORP. (CA)

( * ) Notice: Subject to any disclaimer, the term of this patent is extended or adjusted under 35 U.S.C. 154(b) by 312 days.

(21) Appl. No.: 18/380,441

(22) Filed: Oct. 16, 2023

(65) Prior Publication Data

US 2024/0148696 A1 May 9, 2024

Related U.S. Application Data

(60) Provisional application No. 63/419,136, filed on Oct. 25, 2022.

(51) Int. Cl.

| | |
|---|---|
| ***A61K 31/4184*** | (2006.01) |
| ***A61K 9/16*** | (2006.01) |
| ***A61K 9/19*** | (2006.01) |
| ***A61K 47/40*** | (2006.01) |

(52) U.S. Cl.

CPC ........ *A61K 31/4184* (2013.01); *A61K 9/1694* (2013.01); *A61K 9/19* (2013.01); *A61K 47/40* (2013.01)

(58) Field of Classification Search

CPC .... A61K 31/4184; A61K 9/1694; A61K 9/19; A61K 47/40; A61K 31/724

See application file for complete search history.

(56) References Cited

U.S. PATENT DOCUMENTS

| | | | |
|---|---|---|---|
| 8,076,336 | B2 | 12/2011 | Heinelt et al. |
| 8,076,366 | B2 | 12/2011 | Courvoisier et al. |
| 8,344,006 | B2 | 1/2013 | Drager et al. |
| 8,383,663 | B2 | 2/2013 | Alakhov et al. |
| 8,436,032 | B2 | 5/2013 | Popek et al. |
| 8,436,190 | B2 | 5/2013 | Brittain et al. |
| 8,445,524 | B2 | 5/2013 | Courvoisier et al. |
| 8,461,350 | B2 | 6/2013 | Brittain et al. |
| 8,609,707 | B2 | 12/2013 | Palepu et al. |
| 8,609,863 | B2 | 12/2013 | Brittain et al. |
| 8,669,279 | B2 | 3/2014 | Cooper et al. |
| 8,703,964 | B2 | 4/2014 | Popek et al. |
| 8,791,270 | B2 | 7/2014 | Brittain et al. |
| 8,883,836 | B2 | 11/2014 | Cooper et al. |
| 8,895,756 | B2 | 11/2014 | Brittain et al. |
| 9,000,021 | B2 | 4/2015 | Sundaram et al. |
| 9,034,908 | B2 | 5/2015 | Sundaram |
| 9,144,568 | B1 | 9/2015 | Sundaram |
| 9,265,831 | B2 | 2/2016 | Palepu et al. |
| 9,533,955 | B2 | 1/2017 | Cooper et al. |
| 9,572,796 | B2 | 2/2017 | Palepu et al. |
| 9,572,797 | B2 | 2/2017 | Palepu et al. |
| 9,572,887 | B2 | 2/2017 | Sundaram |
| 9,579,384 | B2 | 2/2017 | Sundaram et al. |
| 9,597,397 | B2 | 3/2017 | Sundaram |
| 9,597,398 | B2 | 3/2017 | Sundaram |
| 9,597,399 | B2 | 3/2017 | Sundaram |
| 10,010,533 | B2 | 7/2018 | Palepu et al. |
| 10,052,385 | B2 | 8/2018 | Sundaram |
| 11,103,483 | B2 | 8/2021 | Palepu et al. |
| 2022/0304983 | A1 | 9/2022 | Jing et al. |

OTHER PUBLICATIONS

Öztekin et al., Journal of Pharmaceutical and Biomedical Analysis, 37 (2005) 1121-1124 (Year: 2005).*

Gust, R., and Krauser, R., "Investigations on the Stability of Bendamustin, a Cytostatic Agent of the Nitrogen Mustard Type, I. Synthesis, Isolation, and Characterization of Reference Substances," *Monatshefte Für Chemic*, 128291-299 (1997).

Maas, B., et al., "Stability of Bendamustine Hydrochloride in Infusions," *Pharmazie*, 49(H.10):775-777 (1994), includin English translation.

Ribosepharm GmbH, "Ribomustin®: bendamustine. Product Monograph," 58 pages (2002).

Teagarden, D.L., and Baker, D.S., "Practical aspects of lyophilization using non-aqueous co-solvent systems," *European Journal of Pharmaceutical Sciences*, 15:115-133 (2002).

Notification of Transmittal; and International Search Report and The Written Opinion of The International Searching Authority, or The Declaration received in PCT Application No. PCT/US2023/077164, dated Jan. 19, 2024 (12 pages).

Gaidhani, K.A., et al., "Lyophilization/Freeze Drying—A Review," *World Journal of Pharmaceutical Research*, 4(8):516-543 (2015).

International Preliminary Report on Patentability (IPRP; PCT/IB/373) issued on Apr. 29, 2025 in PCT Application No. PCT/US2023/077164, including the Notification Concerning Transmittal of IPRP (PCT/ISA/326), mailed May 8, 2025 and English-language Written Opinion (PCT/ISA/237), issued on May 2, 2025) (10 pages).

Communication pursuant to Article 94(3) EPC issued for European Application No. 238090260, dated Mar. 11, 2026 (10 pages).

Troev, K.D., "Poly(alkylene H-phosphonate)s," *Polyphosphoesters Chemistry and Application*, Elsevier Inc., p. 97 (Jan. 30, 2012).

* cited by examiner

*Primary Examiner* — San Ming R Hui

(74) *Attorney, Agent, or Firm* — Crowell & Moring LLP

(57) ABSTRACT

Described herein are lyophilized compositions comprising bendamustine and sulfobutylether beta-cyclodextrin (SBECD) which (a) comprise a molar excess of SBECD relative to bendamustine; (b) do not contain mannitol; and (c) possess a water content of less than about 1% by weight. Such compositions may be prepared in the form of a well-formed cake and exhibit desirable storage stability. The lyophilized compositions can be quickly reconstituted and then be rapidly administered to cancer patients with reduced sodium and/or sugar intake. In addition, a method of treating cancer patients with the described compositions and methods for preparing the lyophilized compositions are described.

14 Claims, No Drawings

LYOPHILIZED BENDAMUSTINE-CYCLODEXTRIN COMPOSITION

RELATED APPLICATIONS

The present patent document claims the benefit of the filing date under 35 U.S.C. § 119(e) of Provisional U.S. Patent Application Ser. No. 63/419,136, filed Oct. 25, 2022, which is hereby incorporated by reference.

BACKGROUND

Field of the Invention

Described herein are lyophilized compositions comprising bendamustine and sulfobutylether beta-cyclodextrin (SBECD) which: (a) comprise a molar excess of SBECD relative to bendamustine; (b) do not contain mannitol; and (c) possess a water content of less than about 1% by weight. Such compositions may be prepared in the form of a well-formed cake and exhibit desirable storage stability. The lyophilized compositions described herein can be quickly reconstituted and then be rapidly administered to cancer patients with reduced sodium and/or sugar (dextrose) intake. In other aspects, described herein are treatments of patients with the described compositions; as well as methods for preparing the described lyophilized compositions.

Background

Bendamustine, 4-[5-[Bis(2-chloroethyl)aminol-1-methylbenzimidazol-2-yl]butanoic acid, is a nitrogen mustard compound, which has been found to be useful in the treatment of leukemia and lymphomas, particularly Chronic Lymphocytic Leukemia (CLL) and Indolent Non-Hodgkin Lymphoma (iNHL). Further, as is disclosed in U.S. Pat. No. 8,703,964 (Popek et al.), bendamustine in complex form has been shown to be effective against solid tumors, including lung cancer, breast cancer and multiple myeloma.

Bendamustine is highly reactive with water and, therefore, commercial formulations of bendamustine are often lyophilized so that they can be stored for longer periods of time. Thus, U.S. Pat. No. 8,791,270 (Brittain et al.) notes that due to its degradation in aqueous solutions (like other nitrogen mustards), bendamustine is supplied as a lyophilized product.

The reactivity of bendamustine with water can also impact the storage stability of a lyophilized bendamustine composition, as residual water will react with the active ingredient over time, resulting in a degradation of the stored product over time. As is noted in U.S. Pat. No. 8,791,270, the primary degradant of lyophilized bendamustine is HP1, also designated as impurity E, a compound having the formula:

(HP1)

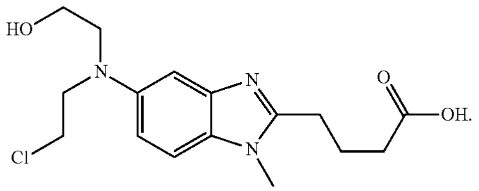

U.S. Pat. No. 8,791,270 further describes that although the addition of a cryoprotectant is not required to produce a lyophilized product (see Column 17, lines 43-46), the addition of mannitol is necessary to produce a commercially acceptable material. For example, the commercial product Treanda® for Injection (see, e.g., U.S. Pat. No. 8,791,270) contains 170 mg/vial of mannitol.

The production of a well-formed durable cake is critical, as the breakage of a cake during storage/processing could lead to particles of the active ingredient becoming attached to the stopper of the lyophilized vial; such particle may remain attached during reconstitution with the result that a lower and/or inconsistent dosage of active ingredient is administered. Furthermore, a poorly formed cake may be evidence that a mixture of several polymorphs is present; this too could result in a situation wherein the storage stability, reconstitution time and other important physical properties of such cakes may be inconsistent from vial to vial. For example, U.S. Pat. No. 8,076,366 (Courvoisier et al.), directed to polymorphs of bendamustine free base, indicates that by varying the form of an active pharmaceutical ingredient, it is possible to vary the physical properties (e.g., shelf-life, bioavailability, morphology, vapor pressure, density, color, and compressibility) of polymorphs of bendamustine.

U.S. Pat. No. 8,791,270 additionally mentions that mannitol can decrease the solubility of bendamustine (at 15 mg/mL) in both ethanol and TBA aqueous solutions. The result is that formulations following the disclosure of U.S. Pat. No. 8,791,270 are nearly fully saturated when reconstituted at room temperature, and therefore must be delivered over an extended period of time in order to minimize the risk of precipitation. Thus, Treanda® for Injection is typically infused intravenously at 100 $mg/m^2$ over 30 minutes for CLL; and infused intravenously at 120 $mg/m^2$ over 60 minutes for iNHL.

U.S. Pat. No. 9,000,021 (Sundaram et al.) discloses a liquid composition of bendamustine that can be administered in much lower doses and therefore much more rapidly than saturated compositions. As a consequence, the commercial formulation covered by U.S. Pat. No. 9,000,021, Bendeka®, can be administered much more rapidly than more fully saturated formulations, such as Treanda® for Injection. Thus, Bendeka® is typically infused intravenously at 100 $mg/m^2$ over 10 minutes for CLL; and infused intravenously at 120 $mg/m^2$ over 10 minutes for iNHL. In order to obtain such higher solubility, Bendeka® employs organic solvents including monothiogylcerol, polyethylene glycol and propylene glycol.

U.S. Pat. Nos. 8,436,032 and 8,703,964, both by Popek et al., disclose compositions comprising bendamustine, a charged cyclodextrin (preferably sulfobutylether beta cyclodextrin or "SBECD"), and optionally a stabilizing agent having a charge opposite to that of the cyclodextrin. These publications indicate that such compositions may be freeze dried/lyophilized—however, the only example showing a lyophilized product (Example 21) includes mannitol. Somewhat similarly, U.S. Pat. No. 8,383,663 (Alakhov et al.) discloses compositions wherein the stabilizing agent is a charged cyclodextrin; while no lyophilization is exemplified in such patent, it is noteworthy that all of the exemplified formulations all contain mannitol.

SUMMARY

It has been unexpectedly found that compositions comprising bendamustine and SBECD can be lyophilized in the absence of mannitol to produce drug formulations that exhibit unexpectedly superior storage stability, can be rapidly reconstituted in a number of pharmaceutically acceptable solvents, and can be rapidly administered to cancer patients with reduced sodium and/or sugar (dextrose) intake.

In one aspect described herein is a lyophilized composition comprising bendamustine and sulfobutylether beta-cyclodextrin, characterized in that such composition: a) comprises a molar excess of sulfobutylether beta-cyclodextrin relative to the amount of bendamustine present; b) does not contain mannitol; and c) has a water retained water content of less than about 1% by weight.

In another aspect described herein is a method for preparing a lyophilized composition comprising bendamustine and sulfobutylether beta-cyclodextrin, the method comprising the steps of: a) preparing an aqueous composition comprising water, bendamustine and sulfobutylether beta-cyclodextrin, wherein the aqueous composition does not contain mannitol; b) transferring the aqueous composition into a vial; c) freezing and annealing the aqueous composition to form a frozen and annealed composition; and d) subjecting the frozen and annealed composition to a lyophilization cycle comprising: i) a first drying step conducted at between about −5° and about −50° C. at a pressure of between about 75 and 150 mTorr; and ii) a second drying step conducted at between about 5° and about 50° C. at a pressure of less than about 25 mTorr.

In yet another aspect described herein is a method for treating a cancer patient with an effective dose of the described composition, which has been reconstituted from a lyophilized composition comprising bendamustine and sulfobutylether beta-cyclodextrin, characterized in that such composition: a) comprises a molar excess of sulfobutylether beta-cyclodextrin relative to the amount of bendamustine present; b) does not contain mannitol; and c) has a water retained water content of less than about 1% by weight.

DETAILED DESCRIPTION OF THE DRAWINGS AND THE PRESENTLY PREFERRED EMBODIMENTS

It has been unexpectedly found that compositions comprising bendamustine and SBECD can be lyophilized in the absence of mannitol to produce drug formulations that exhibit unexpectedly superior storage stability, can be rapidly reconstituted in a number of pharmaceutically acceptable solvents and can be rapidly administered to cancer patients with reduced sodium and/or sugar (dextrose) intake.

In one aspect, described herein is a lyophilized composition comprising bendamustine and sulfobutylether beta-cyclodextrin ("SBECD") characterized in that the lyophilized composition comprises a molar excess of sulfobutylether beta-cyclodextrin relative to the amount of bendamustine present; does not contain mannitol; and has a water content of less than about 1.0% by weight.

When bendamustine is combined with SBECD is an aqueous environment, the compounds form an inclusion complex in a 1:1 molar ratio. In forming such inclusion complex, the bendamustine moiety interacts with and becomes sheltered within the cavity of the torus-like structure formed by the cyclic cyclodextrin units of SBECD, thereby sheltering the bendamustine moiety from the degrading effects of an aqueous environment.

In order to provide a composition which is amenable to rapid administration to cancer patients, it is necessary to ensure that the bendamustine moiety is not fully saturated in the reconstituted solution at room temperature. Accordingly, in certain embodiments, the described compositions may comprise a molar excess of SBECD, which ensures that all of the bendamustine precursor will remain in complex form (and will not precipitate) during the infusion process. Preferably, the molar ratio of bendamustine to SBECD is between about 1:2 and about 1:25; more preferably, between about 1:3 and about 1:15; even more preferably, between about 1:4 and about 1:10; and most preferably, between about 1:5 and about 1:7.

Importantly, the described composition does not contain mannitol, as this excipient can lower the solubility of bendamustine in aqueous environments. Preferably, the described compositions do not further comprise any other or similar cryoprotectant compound(s), which would also have a similar adverse effect upon bendamustine solubility.

In certain embodiments, while the described composition may contain further excipients, such as soluble polymers, for example, polyoxyethylene, poloxamers, polyvinylpyrrolidone, and dextran; salts including, without limitation, sodium chloride, magnesium chloride, and calcium chloride; and lipids including, without limitation, fatty acids, glycerol fatty acid esters, glycolipids, phospholipids; the addition of such excipients is not required to produce a pharmaceutically acceptable formulation in many instances.

In some embodiments, the described compositions may further comprise cationic stabilizing agents, such as those described in U.S. Pat. No. 8,436,032 (Popek et al) and U.S. Pat. No. 8,383,663 (Alakhov et al). Exemplary cationic agents, which may be employed, include tertiary or quaternary ammonium compounds, such as N-alkyl-N,N-dimethylamines, N-alkyl-N,N-diethylamines, N-alkyl-N—N-diethanoloamines, N-alkylmorpholine, N-alkylpiperidine, N-alkylpyrrolidine, N-alkyl-N,N,N-trimethylammonium, N,N-dialkyl-N,N-dimethylammonium, N-alkyl-N-benzyl-NN-diimethylammonium, N-alkyl-pyridinium, N-alkyl-picolinium, alkylamidomethylpyridinium, carbalkoxypyridinium, N-alkylquinolinium, N-alkylisoquinolinium. N,N-alkylmethylpyrollidinium, and 1-alkyl-2,3-dimethylimidazolium. Particularly preferred cationic adjuvants include sterically hindered tertiary amines, such as N-alkyl-N—N-diisopropylamine, N-alkylmorpholine, N-alkylpiperidine, and N-alkylpyrrolidine; and quaternary ammonium compounds such as cetylpyridinium chloride, benzyldimethyldodecylammonium chloride, dodecylpyridinium chloride, hexadecyltrimethylammonium chloride, benzyldimethyltetradecylammonium chloride, octedecyldimethylbenzylammonium chloride, and domiphen bromide.

Polycationic compounds such as oligo- or polyamines, or pegylated oligo- or polyamines may also be employed in the described compositions, as the stabilizing agent. Preferred polycationic compounds include oligoamines, such as spermin, spermidin, putrescine, and cadaverine; polyamines: such as polyethyleneimine, polyspermin, polyputrescine, and polycadaverine; and pegylated oligoamines and polyamines of the group listed above. Particularly preferred is PI2080, polyethyleneimine 2000 conjugated with PEG 8000.

One preferred class of cationic stabilizing agents are polypeptides comprising from about 5 to about 50, more preferably between about 6 and about 20, amino acids; wherein at least about 50% of such amino acids contain a positive charge. Most preferably, such charged amino acids are argenine. Particularly preferred members of this class include polyargenine and protamine which has been digested with thermolysin (hereinafter referred to as Low Molecular Weight Protamine or "LMWP").

In certain embodiments, hydrophobically modified oligo- or polyamines may also be employed. Preferred stabilizing agent of this type include, e.g., acetyl spermin, acetyl polyspermin, acetyl polyethyleneimine, butyryl spermin, butyryl polyspermin, butyryl polyethyleneimine, lauroyl spermin, lauroyl polyspermin, lauroyl polyethyleneimine, stearoyl spermin, stearoyl polyspermin, and stearoyl polyethyleneimine.

In addition, in certain embodiments, cationic polysaccharides and synthetic polycationic polymers may also be employed in the described compositions. Exemplary cationic polysaccharides include, e.g., chitosan, deacetylated chitosan, quaternized cellulose, quaternized amylase, quaternized amylopectine, quaternized partially hydrolyzed cellulose, quaternized partially hydrolyzed amylase and quaternized partially hydrolyzed amylopectine. Examples of synthetic polycationic polymers include, e.g., polyquaternium 2 (poly[bis(2-chloroethyl]ether-alt-1,3-bis[3-dimethylamino)propyl]-urea, quaternized); polyquaternium 11 (poly(1-vinylpyrrolidone-co-dimethylammonioethyl methacrylate) quaternized); polyquaternium 16 and 44 (copolymer of vinylpyrrolidone, and quaternized vinylimidazole); and polyquaternium 46 (copolymer of vinylcaprolactam, vinylpyrrolidone, and quaternized vinylimidazole).

Although the cationic cyclopolysaccharides that may be employed as stabilizing agents may comprise any one or mixture of cationic groups, in general it is preferred that such compound comprise an amino, a guanidine or a quaternary ammonium group. Exemplary amino-cyclodextrins, which may be preferably employed, include, e.g., amino-alpha-cyclodextrincyclodextrins, amino-beta-cyclodextrin-cyclodextrins, and amino-gamma-cyclodextrin, each cyclodextrins, preferably having a substitution level of between about 4 and about 10. Preferred amino-cyclodextrins of this type include hexakis(6-amino-6-deoxy) alpha-cyclodextrin, heptakis(6-amino-6-deoxy) beta-cyclodextrin, octakis(6-amino-6-deoxy) gamma-cyclodextrin and heptakis(6-amino-6-deoxy) beta-cyclodextrin. Other cationic cyclopolysaccharides which may be employed including guanidino-cyclodextrins, preferably having a substitution level of between about 4 and about 10, with heptakis(6-guanidino-6-deoxy) beta-cyclodextrin being particularly preferred; and alkylamino-cyclodextrins, preferably having a substitution level of between about 4 and about 10, with as 6-deoxy-6-(3-hydroxy)propylamino beta-cyclodextrin being particularly preferred; and ammonium-cyclodextrins, preferably having a substitution level between 4 and 9, such as 2-hydroxy-N,N,N-trimethylpropanammonium-cyclodextrin.

In certain embodiments, particularly preferred cationic polysaccharides include, e.g., hexakis(6-amino-6-deoxy) alpha-cyclodextrin, heptakis(6-amino-6-deoxy) beta-cyclodextrin, octakis(6-amino-6-deoxy) gamma-cyclodextrin, heptakis(6-guanidino-6-deoxy) beta-cyclodextrin, octakis (6-guanidino-6-deoxy)-gamma-cyclodextrin, 2-hydroxy-N,N,N-trimethylpropanammonium-cyclodextrin and 6-deoxy-6-(3-hydroxy)propylamino beta-cyclodextrin; with 6-deoxy-6-(3-hydroxy)propylamino beta-cyclodextrin being especially preferred.

When present, the stabilizing agent may be present in a molar ratio of between about 5:1 and about 1:1000; preferably, of between about 1:4 and about 1:100, based upon the molar amount of SBECD present.

In certain embodiments, the described compositions possess a water content of less than about 1.0% by weight. Preferably, such compositions possess a water content of less than 0.75% by weight; and more preferably, a water content of less than about 0.6% by weight. Although essentially dry compositions can be prepared by increasing the duration of the lyophilization cycle, compositions with very small amounts of retained water (in excess of about 0.2% or about 0.34% by weight) exhibit desirable long-term storage stability.

In another aspect, described herein is a method for preparing the described lyophilized composition, wherein the composition comprises bendamustine and sulfobutylether beta-cyclodextrin. The method comprises the steps of:

a) preparing an aqueous composition comprising water, bendamustine and sulfobutylether beta-cyclodextrin, which does not contain mannitol;
b) transferring the aqueous composition into a vial;
c) freezing and annealing the aqueous composition to form a frozen and annealed composition; and
d) subjecting the frozen and annealed composition to a lyophilization cycle comprising:
i) a first drying step conducted at between about −5° C. and about −50° C. at pressure of between about 75 and about 150 mTorr; and
ii) a second drying step conducted at between about 5° C. and about 50° C. at pressure of less than about 25 mTorr.

The aqueous composition of step a) may be prepared by the dissolution of a solid bendamustine precursor, such as bendamustine hydrochloride and/or bendamustine hydrochloride monohydrate in an aqueous solution of SBECD; or by mixing an aqueous solution of SBECD with an aqueous stock solution of bendamustine. As is noted above, the molar ratio of bendamustine to SBECD may be between about 1:2 and about 1:25; more preferably, between about 1:3 and about 1:15; even more preferably, between about 1:4 and about 1:10; and most preferably, between about 1:5 and about 1:7.

The aqueous composition of step a) is vigorously mixed and, optionally, may be subjected to the action of ultrasound waves to obtain a homogenous and equilibrated aqueous solution. In certain preferred embodiments, the aqueous solution of SBECD used for the preparation of the described composition may contain at least 4% of SBECD; and more preferably, such solution contains at least 10% of SBECD.

In certain embodiments, the stabilizing agent and excipient (if either or both are present) are preferably introduced to the composition by their addition to a pre-prepared aqueous homogenous and equilibrated solution of bendamustine with SBECD. These agents may be added either as pure substances or as aqueous solutions, and are preferably mixed employing gentle agitation.

The homogenous and equilibrated aqueous solution may then be aseptically filtered into a sterile container, filled into an appropriately sized vial, partially stoppered and loaded into the lyophilizer. The solution is then lyophilized to produce the described composition.

The vial employed in step b) and the stopper which is present to partially seal the vial are composed of materials, which are suitable for the lyophilization process and which exhibit chemical resistance to the pre-lyophilizate solution. Such materials are well known to those of skill in the art and are commercially available. Most preferably, a 25 cc/20 mm type 1 amber glass vial, fitted with a 20 mm chlorobutyl fluoropolymer coated lyophilization stopper and sealed with an orange-colored Flip-Off® aluminum overseal may be used in the described method.

The freezing/annealing step is typically conducted at between about −20° C. and about −50° C. until the pre-lyophilizate solution is fully frozen and annealed. The time required to perform the freezing/annealing step will depend upon a number of parameters, including the size of the sample, the precise composition of the sample and the efficiency of the equipment employed. In certain embodiments, the times range from 3 hours or less to 10 hours or more. However, the optimal time for any particular set of parameters can be determined by one of skill in the art using routine experimentation.

The first drying step is typically conducted at between about −5° C. and about −50° C. at pressure of between about 75 and about 150 mTorr. Preferably, such step is conducted at between about −20° C. and about −40° C.; and at pressure of between about 100 and about 145 mTorr. The time required to perform the first drying step will depend upon a number of parameters, including the size of the sample, the precise composition of the sample, the particular temperature and pressure selected, and the efficiency of the equipment employed. In certain embodiments, the times run for 10 hours or less to 72 hours or more. However, the optimal time for any particular set of parameters can be determined by one of skill in the art using routine experimentation.

The second drying step may be conducted at between about 5° C. and about 50° C. at pressure of of less than about 25 mTorr. Preferably, such step is conducted at between about 10° C. and about 40° C.; and at pressure of less than about 15 mTorr. This second drying step is preferably conducted until the composition has a water content of less than about 1.0% by weight; preferably of less than about 0.75% by weight; and most preferably of less than about 0.6% by weight. Although essentially dry compositions can be prepared by increasing the duration of the lyophilization cycle, compositions with very small amounts of retained water (in excess of about 0.1% or about 0.2% by weight) exhibit desirable long-term storage stability.

The time required to perform the second drying step will depend upon a number of parameters, including the size of the sample, the precise composition of the sample, the particular temperature and pressure selected, and the efficiency of the equipment employed. In certain embodiments, the times run for 10 hours or less to 60 hours or more. However, the optimal time for any particular set of parameters can be determined by one of skill in the art using routine experimentation.

In yet another aspect, described herein is a method for treating a cancer patient comprising administering to the cancer patient an effective dose of the described composition reconstituted from a lyophilized composition described herein, comprising bendamustine and sulfobutylether beta-cyclodextrin, characterized in that the composition comprises a molar excess of sulfobutylether beta-cyclodextrin relative to the amount of bendamustine present; does not contain mannitol; and has a water content of less than about 1.0% by weight.

In one embodiment, a 25 mL vial containing the lyophilized composition described herein may be prepared by complexing 104.56 mg of bendamustine hydrochloride monohydrate with 3.33 g of SBECD in an aqueous solution, such each vial contains 90.76 mg of bendamustine moiety in complex form [an amount equivalent to the amount of bendamustine moiety present in 100 mg of bendamustine hydrochloride]; and lyophilizing the solution following the method detailed above.

The lyophilized powder is then reconstituted by adding 8.0 mL of a pharmaceutically acceptable diluent. It is noteworthy that, in addition to the diluents used in current commercial formulations of bendamustine (i.e., 0.9% Sodium Chloride Injection; 2.5% Dextrose/0.45% Sodium Chloride Injection; and 5% Dextrose Injection), as demonstrated in Example 3, the inclusion complex formulations demonstrate sufficient stability in water such that Water For Injection may additionally be used as a diluent. This can provide additional benefits to patients who suffer from sugar and/or sodium contraindications.

In certain embodiments, the recommended dosage for the described compositions for CLL is 100 mg/$m^2$ of bendamustine hydrochloride administered intravenously over 10 minutes on Days 1 and 2 of a 28-day cycle, up to 6 cycles. The recommended dosage for iNHL is 120 mg/$m^2$ of bendamustine hydrochloride administered intravenously over 10 minutes on Days 1 and 2 of a 21-day cycle, up to 8 cycles.

The amount of reconstituted solution necessary to achieve the required dose is then typically added to a 150 mL partial additive bag (PAB) containing 50 mL of the same diluent that was used for reconstitution. Prior to administration, the PAB contents are mixed by gently inverting the bag back and forth 20 times.

In certain embodiments, for CLL indication the volume of the dosing solution in the PAB ranges from 60 mL for a 1 $m^2$ patient to 80 mL for a 3 $m^2$ patient and the corresponding bendamustine concentrations range from 1.51 mg/mL for a 1 $m^2$ patient to 3.4 mg/mL for a 3 $m^2$ patient; which are equivalent to 1.67 mg/mL to 3.75 mg/mL of bendamustine hydrochloride, respectively.

In certain embodiments, for iNHL indication the admixture ranges from 62 mL for a 1 $m^2$ patient to 86 mL for a 3 $m^2$ patient and the corresponding bendamustine concentrations range from 1.76 mg/mL for a 1 $m^2$ patient to 3.80 mg/mL for a 3 $m^2$ patient; which are equivalent to 1.94 mg/mL to 4.19 mg/mL of bendamustine hydrochloride, respectively.

Because the reconstituted formulations are not fully saturated, the compositions may be administered in less than about 15 minutes, preferably in less than about 10 minutes.

It is to be understood that each component, compound, substituent, or parameter disclosed herein is to be interpreted as being disclosed for use alone or in combination with one or more of each and every other component, compound, substituent, or parameter disclosed herein.

The terms "composition" and "formulation" are used herein interchangeably.

It is also to be understood that each amount/value or range of amounts/values for each component, compound, substituent, or parameter disclosed herein is to be interpreted as also being disclosed in combination with each amount/value or range of amounts/values disclosed for any other component (s), compounds(s), substituent(s), or parameter(s) disclosed herein and that any combination of amounts/values or ranges of amounts/values for two or more component(s), compounds(s), substituent(s), or parameters disclosed herein are thus also disclosed in combination with each other for the purposes of this description.

It is further understood that each lower limit of each range disclosed herein is to be interpreted as disclosed in combination with each upper limit of each range disclosed herein for the same component, compounds, substituent, or parameter. Thus, a disclosure of two ranges is to be interpreted as a disclosure of four ranges derived by combining each lower limit of each range with each upper limit of each range. A disclosure of three ranges is to be interpreted as a disclosure of nine ranges derived by combining each lower limit of each range with each upper limit of each range, etc. Furthermore, specific amounts/values of a component, compound, substituent, or parameter disclosed in the description or an example is to be interpreted as a disclosure of either a lower or an upper limit of a range and thus can be combined with any other lower or upper limit of a range or specific amount/value for the same component, compound, substituent, or parameter disclosed elsewhere in the application to form a range for that component, compound, substituent, or parameter.

EXAMPLES

The following examples are provided to illustrate the described compositions and methods, but are not to be construed as limiting in any way except as indicated in the appended claims.

Examples 1 and 2; and Comparative Experiments A-G

Lyophilization Method

The following method was employed for each of Examples 1 and 2 and Comparative Experiments A-F:

A 100 mL bulk solution of bendamustine/SBECD complex was prepared by:

(a) adding 70 mL of water for injection to a 100 mL volumetric flask;

(b) slowly adding 35.38 grams of SBECD and stirring for 5 minutes at 5° C. until a clear solution was obtained;

(c) slowly adding 1.04 grams of bendamustine hydrochloride monohydrate and stirring for 30 minutes at 5° C. until a clear solution was obtained; and (d) adding additional water for injection until the total volume was 100 mL.

10 mL of the bulk solution were transferred into a 25 mL glass, type 1, flint vial; and partially sealed with a 20 mm butyl rubber stopper. The vials were placed inside a lab scale Millrock REVO Series Freeze Dryer lyophilizer; and subjected to the lyophilization cycle listed in Table 1 below.

The water content of the resultant lyophilized materials was determined (average of 10 samples). The results of such testing are also provided in Table 1 below.

TABLE 1

| Example or Comparative Experiment | Primary Drying Temperature/Time | Primary Pressure mTorr | Secondary Drying Temperature/Time | Secondary Pressure mTorr | Water Content (wt %) |
|---|---|---|---|---|---|
| A | −30° C./2600 min | 338 | 5° C./500 min | 203 | N/A* |
| | −10° C./100 min | 203 | 25° C./600 min | 203 | |
| B | −15° C./3000 min | 100 | 25° C./900 min | 100 | 2.4%** |
| C | −15° C./2800 min | 100 | 30° C./1200 min | 100 | 1.59% |
| | −5° C./1000 min | 100 | | | |
| D | −15° C./2800 min | 100 | 30° C./1560 min | 100 | 1.1% |
| | −5° C./690 min | 100 | | | |
| E | −15° C./3680 min | 100 | 25° C./1020 min | 100 | 1.36% |
| 1 | −15° C./ 3680 min | 100 | 25° C./1020 min | 100 | 0.72% |
| | | | 20° C./2880 min | 3 | |
| 2 | −15° C./3680 min | 100 | 32° C./2240 min | 5 | 0.5% |

*Water content could not be measured as sample would not dissolve in nonpolar medium.

**Average of 3 replications.

The data above shows that the water content of the lyophilized cake can be reduced to below 1% employing a lyophilization cycle that includes a low temperature primary drying step followed by a very low pressure secondary drying step.

The lyophilized cake of Example 1 showed some aesthetic imperfection cracking, but did not show any critical defects or imperfections. Upon the addition of 8 mL water for injection, the cake dissolved in less than 1 minute (average of 3 samples).

The lyophilized cake of Example 2 was hard and compact with a uniform internal structure. Upon the addition of 8 mL 0.9% saline solution, the cake dissolved in about 2 minutes (average of 3 samples).

Storage Stability

The storage stability of samples of Comparative Experiments B and D as well as of Example 1 was determined by storing the samples upright at 40° C. (+/−2° C.) and 75% relative humidity (+/−5% relative humidity) for 6 months. The average reduction in total bendamustine content (3 samples) was determined, and the effective shelf-life of the samples (when stored at the conditions above) calculated based upon the estimated time until the HP1 content exceeded 1.5% by weight) and the results are presented in Table 2 below:

TABLE 2

| Sample | Initial Water Content (determined above) | Decrease in Bendamustine Concentration | Estimated Shelf Life (Months) |
|---|---|---|---|
| B | 2.4% | 1.8% | 20.1 |
| D | 1.1% | 1.3% | 32.0 |
| 1 | 0.7% | 0.6% | 47.2 |

The degree of degradation is greatly reduced in lyophilized bendamustine compositions having less than about 1% by weight of retained water.

The above results demonstrate that reducing the initial water content of the lyophilizate greatly increases the storage stability of the composition.

Example 3—Stability in Water for Injection

Vials of lyophilized powder containing 90.76 mg bendamustine in complex with SBECD, produced in accordance with the methods described herein, were stored at room temperature (25±5° C.) for 13 months.

The lyophilized material was first reconstituted by adding 8 mL of water for injection (WFI) to each vial to produce 10 mL of reconstituted solution. 10 mL of such reconstituted solution was added to a 150 mL PAB infusion bag containing an additional 50 mL of WFI to produce a dosing solution.

Such WFI dosing solutions were stored either (a) under refrigerated conditions (5±3° C.) or (b) at room temperature (25±5° C.); with aliquots being periodically removed as indicated in the Table below. Such aliquots were evaluated using HPLC to determine their HP1 concentration. As is discussed above, HP1 is the primary degradant of bendamustine in aqueous environments; testing has shown that bendamustine compositions containing about 5% of less by weight of HP1 are suitable for administration to humans.

The results of such testing are summarized below:

TABLE 3

| Percentage of HP1 in Dosing Solutions containing Water for Injection: | | | | | |
|---|---|---|---|---|---|
| At 5 ± 3° C.: | | | | | |
| 0 Hours | 24 Hours | 48 Hours | 120 Hours | 7 Days | |
| 0.66 | 0.79 | 0.95 | 1.44 | 1.70 | |
| At 25 ± 5° C. | | | | | |
| 0 Hours | 3 Hours | 6 Hours | 12 Hours | 24 Hours | 48 Hours |
| 0.66 | 0.82 | 1.14 | 1.18 | 2.91 | 5.15 |

The above data indicate that the described compositions exhibit stability in WFI such that WFI can be employed as a diluent for human patients.

The invention claimed is:

1. A lyophilized composition comprising bendamustine and sulfobutylether beta-cyclodextrin, characterized in that the composition:

a) has a molar ratio of bendamustine to sulfobutylether beta-cyclodextrin of between about 1:4 and about 1:10;

b) does not contain mannitol; and c) has a retained water content of less than about 1% by weight.

2. The composition of claim 1, wherein the composition has a water content of less than about 0.75% by weight.

3. The composition of claim 2, wherein the composition has a water content of less than about 0.6% by weight.

4. The composition of claim 1, wherein the composition has a water content of less than about 1.0% and more than 0.2% by weight.

5. The composition of claim 3, wherein the composition has a water content of less than about 0.6% and more than 0.4% by weight.

6. The composition of claim 1, wherein the molar ratio of bendamustine to sulfobutylether beta-cyclodextrin is between about 1:5 and about 1:7.

7. The composition of claim 1, wherein the composition further comprises a cationic stabilizing agent.

8. A method for preparing a lyophilized composition for administration to a cancer patient, the method comprising the steps of:

a) preparing an aqueous composition comprising water, bendamustine and sulfobutylether beta-cyclodextrin in a molar ratio of bendamustine to sulfobutylether beta-cyclodextrin of between about 1:4 and about 1:10, and which does not contain mannitol;

b) transferring the aqueous composition into a vial;

c) freezing and annealing the aqueous composition to produce a frozen and annealed composition; and d) subjecting the frozen and annealed composition to a lyophilization cycle comprising:

i) a first drying step conducted at between about −5° and about −50° C. at a pressure of between about 75 and 150 mTorr; and ii) a second drying step conducted at between about 5° and about 50° C. at a pressure of less than about 25 mTorr, until such composition has a retained water content of less than about 1% by weight.

9. The method of claim 8, wherein the first drying step is conducted between about −20° C. and about −40° C.; and at pressure of between about 100 and about 145 mTorr.

10. The method of claim 8, wherein the second drying step is at between about 10° C. and about 40° C.; and at pressure of less than about 15 mTorr.

11. A method for treating a cancer patient, comprising administering to the cancer patient an effective dose of a composition reconstituted from a lyophilized composition comprising bendamustine and sulfobutylether beta-cyclodextrin and characterized in that the lyophilized composition a) has a molar ratio of bendamustine to sulfobutylether beta-cyclodextrin of between about 1:4 and about 1:10;

b) does not contain mannitol; and c) has a retained water content of less than about 1% by weight.

12. The method of claim 11, wherein the composition is administered in about 15 minutes or less.

13. The method of claim 11, wherein water for injection is employed as a diluent.

14. A lyophilized composition comprising bendamustine and sulfobutylether beta-cyclodextrin, characterized in that the composition: a) comprises a molar excess of sulfobutylether beta-cyclodextrin relative to the amount of bendamustine present; b) does not contain mannitol; c) has a retained water content of less than about 1% by weight; and d) further comprises a cationic stabilizing agent, wherein the cationic stabilizing agent is 6-deoxy-6-(3-hydroxy) propylamino beta-cyclodextrin.

* * * * *